United States Patent
Roh et al.

(10) Patent No.: US 11,565,399 B2
(45) Date of Patent: Jan. 31, 2023

(54) WEARABLE HAND ROBOT

(71) Applicant: REPUBLIC OF KOREA (NATIONAL REHABILITATION CENTER), Seoul (KR)

(72) Inventors: Sung Jun Roh, Seoul (KR); Byeong Geol Park, Icheon-si (KR); Hyo Seok Yi, Yongin-si (KR); Kyu Jin Cho, Seoul (KR); Brian Byunghyun Kang, Seoul (KR); Hyung Min Choi, Seoul (KR); Sun Cheol Kwon, Seoul (KR)

(73) Assignee: REPUBLIC OF KOREA (NATIONAL REHABILITATION CENTER), Seoul (KR)

( * ) Notice: Subject to any disclaimer, the term of this patent is extended or adjusted under 35 U.S.C. 154(b) by 188 days.

(21) Appl. No.: 16/881,740

(22) Filed: May 22, 2020

(65) Prior Publication Data

US 2020/0324402 A1    Oct. 15, 2020

Related U.S. Application Data (63) Continuation of application No. PCT/KR2018/014551, filed on Nov. 23, 2018.

(30) Foreign Application Priority Data

Nov. 23, 2017  (KR) .................. 10-2017-0157211

(51) Int. Cl.
   *B25J 9/00* (2006.01)
   *A61H 1/02* (2006.01)
   *B25J 1/02* (2006.01)

(52) U.S. Cl.
   CPC .......... *B25J 9/0006* (2013.01); *A61H 1/0288* (2013.01); *B25J 1/02* (2013.01);
   (Continued)

(58) Field of Classification Search
   CPC .......... B25J 9/0006; B25J 1/02; B25J 9/0015; A61H 1/0288; A61H 2201/14; A61H 2201/1638; A61H 2201/165
   See application file for complete search history.

(56) References Cited

U.S. PATENT DOCUMENTS

| 2010/0041521 A1* | 2/2010 | Ingvast .................. B25J 9/0006 482/49 |
| 2012/0029399 A1* | 2/2012 | Sankai ................. A61H 1/0288 601/40 |

(Continued)

FOREIGN PATENT DOCUMENTS

| KR | 10-2012-0012675 A | 2/2012 |
| KR | 10-1263933 B1 | 5/2013 |

(Continued)

OTHER PUBLICATIONS

International Search Report issued in PCT/KR2018/014551; dated Mar. 11, 2019.

*Primary Examiner* — Jennifer Dieterle
*Assistant Examiner* — Aren Patel
(74) *Attorney, Agent, or Firm* — Studebaker & Brackett PC (57) ABSTRACT

The inventive concept relates to a wearable hand robot mounted on a finger to bend the finger by an external force transmitted through a wire. The wearable hand robot is capable of preventing an injury to a user's hand by the wire, achieving simplification of the structure of a finger cap and an improvement in a wearing sensation, and stably moving the finger while having a tactile sensation.

8 Claims, 6 Drawing Sheets

(52) U.S. Cl.
CPC ......... *B25J 9/0015* (2013.01); *A61H 2201/14* (2013.01); *A61H 2201/165* (2013.01); *A61H 2201/1638* (2013.01)

(56) References Cited

U.S. PATENT DOCUMENTS

| | | | |
|---|---|---|---|
| 2012/0289877 A1* | 11/2012 | Hegland | A61F 5/013 602/22 |
| 2013/0219586 A1 | 8/2013 | Ihrke et al. | |
| 2013/0226350 A1* | 8/2013 | Bergelin | A61H 1/0288 2/160 |
| 2014/0303750 A1* | 10/2014 | MacDuff | A61F 2/4241 623/57 |
| 2018/0345481 A1* | 12/2018 | Cho | B25J 9/0006 |
| 2019/0060099 A1* | 2/2019 | Ciocarlic | A41D 19/00 |
| 2019/0209412 A1* | 7/2019 | Lindemann | A61H 1/0288 |
| 2021/0161696 A1* | 6/2021 | Ewaldsson | A61F 5/0118 |

FOREIGN PATENT DOCUMENTS

| | | |
|---|---|---|
| KR | 10-2014-0143557 A | 12/2014 |
| KR | 10-2015-0129919 A | 11/2015 |
| KR | 10-2017-0056722 A | 5/2017 |
| KR | 10-1793906 B1 | 11/2017 |

\* cited by examiner

WEARABLE HAND ROBOT

CROSS-REFERENCE TO RELATED APPLICATIONS

The present application is a continuation of International Patent Application No. PCT/KR2018/014551, filed Nov. 23, 2018, which is based upon and claims the benefit of priority to Korean Patent Application No. 10-2017-0157211, filed on Nov. 23, 2017. The disclosures of the above-listed applications are hereby incorporated by reference herein in their entirety.

BACKGROUND

Embodiments of the inventive concept described herein relate to a wearable hand robot, and more particularly, relate to a wearable hand robot mounted on a finger to bend the finger by an external force transmitted through a wire.

A number of wearable robots have been developed to help people who have the skeletons of bodies, but cannot move parts of their bodies due to nervous disorders such as paralysis.

In particular, a wearable hand robot worn like a glove has been developed to help people who cannot move fingers.

A conventional wearable robot of a glove type generally includes actuators for moving joints of each finger using an exoskeleton structure.

In the case where the actuators are installed on the moving portions of the finger as described above, the volume and the weight of the wearable hand robot are increased. Due to the complex structure, manufacturing cost is also increased. Further, due to the complex structure and the large volume, a user feels an inconvenience to wear and use the wearable hand robot.

Furthermore, the conventional wearable hand robot is formed of a fiber material, and therefore when a wire is pulled, the wire around the finger penetrates into the skin of a hand to cause pain.

Moreover, because the conventional wearable hand robot is formed of the fiber material, the wearable hand robot is easily contaminated by the user's sweat or filth and has to be frequently washed accordingly. In addition, the user cannot use the wearable hand robot while the wearable hand robot is dried.

A conventional wearable hand robot for solving these problems is disclosed in Korean Patent Publication No. 10-2017-0056722.

The conventional wearable hand robot has a structure in which a finger strap is mounted on finger knuckles, a finger cap is mounted on an end of a finger, and a first wire and a second wire pulled or released to bend or unfold the finger are inserted into the finger cap and are disposed to intersect with each other.

That is, to allow the first wire and the second wire inserted into the finger cap to move in the finger cap without interfering with each other, tubes through which the first wire and the second wire move are provided in the finger cap, and therefore the inside of the finger cap has a double or triple structure.

Accordingly, the structure of the finger cap is complicated, and during finger motion, a wearing sensation of the finger cap is lowered, and a user has difficulty in moving the finger while feeling a tactile sensation with a finger tip.

Furthermore, because the finger strap of the conventional wearable robot is mounted on only the finger knuckles, when the finger is moved, the finger strap is raised off the finger knuckles and easily separated from the finger, and accordingly the finger cannot be stably moved.

SUMMARY

Embodiments of the inventive concept provide a wearable hand robot for preventing an injury to a user's hand by a wire, achieving simplification of the structure of a finger cap and an improvement in a wearing sensation, and stably moving a finger while having a tactile sensation.

According to an exemplary embodiment, a wearable hand robot includes at least one first wire disposed to extend toward a distal end portion of a finger and change an extension direction to a direction toward a root of the finger, a second wire disposed to extend toward the distal end portion of the finger along the back of the finger, a finger strap having a plurality of finger holders mutually connected along a lengthwise direction of the finger, in which each of the plurality of finger holders includes a finger mounting part that is mounted on the back of the finger and that forms a second wire passage through which the second wire moves and a pair of finger grips that protrude from the finger mounting part so as to be opposite to each other, have a first wire passage formed therein through which the first wire moves, and grip the finger while partially surrounding the finger, a finger cap that is mounted on the distal end portion of the finger and that includes, on the outside thereof, a wire direction changing part that changes a moving direction of the first wire and a wire fixing part to which a distal end portion of the second wire is fixed, a back-of-hand support part including a second wire guide that guides movement of the second wire, the back-of-hand support part being supported on the back of a hand, and a palm support part including a first wire guide that guides movement of the first wire, the palm support part being supported on a palm of the hand.

Here, the wearable hand robot may further include a mounting means that mounts the back-of-hand support part and the palm support part on the hand.

The mounting means may include a band that connects the back-of-hand support part and the palm support part and that has a plurality of locking recesses formed through the band and a locking protrusion that protrudes from the back-of-hand support part or the palm support part and that is selectively fit into the plurality of locking recesses of the band.

The wearable hand robot may further include a finger tube for a thumb, the finger tube being attached to or detached from the thumb, a band for the finger tube, the band having a plurality of auxiliary locking recesses formed therein, in which the band supports the finger tube for the thumb, and an auxiliary locking protrusion that protrudes from the back-of-hand support part or the palm support part and that is selectively fit into the plurality of auxiliary locking recesses of the band for the finger tube.

The finger strap may include two finger straps mounted on an index finger and a middle finger of a user, respectively, and the first wire may be installed to pass through finger caps and the finger straps mounted on the index finger and the middle finger.

The finger strap may be formed to be stretchable such that an interval between the finger holders adjacent to each other or an interval between the finger cap and the finger holder adjacent to each other is adjusted depending on a length of a user's finger.

The wearable hand robot may further include a tension measurement sensor that is provided on a moving path of at least one of the first wire and the second wire and that measures tension acting on at least one of the first wire and the second wire.

The wearable hand robot may further include a joint angle measurement sensor that is provided on a moving path of at least one of the first wire and the second wire and that measures a joint angle of the finger depending on a length by which at least one of the first wire and the second wire moves.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

The above and other aspects, features, and advantages of the inventive concept will become apparent from the following description of embodiments given in conjunction with the accompanying drawings. However, the inventive concept is not limited to the embodiments disclosed herein and may be implemented in various different forms. Herein, the embodiments are provided to provide complete disclosure of the inventive concept and to provide thorough understanding of the inventive concept to those skilled in the art to which the inventive concept pertains.

Terms used herein are only for description of embodiments and are not intended to limit the inventive concept. As used herein, the singular forms are intended to include the plural forms as well, unless context clearly indicates otherwise. It will be further understood that the terms "comprise" and/or "comprising" specify the presence of stated features, components, and/or operations, but do not preclude the presence or addition of one or more other features, components, and/or operations. In addition, identical numerals will denote identical components throughout the specification, and the meaning of "and/or" includes each mentioned item and every combination of mentioned items.

Unless otherwise defined, all terms (including technical and scientific terms) used herein have the same meaning as commonly understood by those skilled in the art to which the inventive concept pertains. It will be further understood that terms, such as those defined in commonly used dictionaries, should not be interpreted in an idealized or overly formal sense unless expressly so defined herein.

Hereinafter, the inventive concept will be described in detail with reference to the accompanying drawings.

Figure 1:
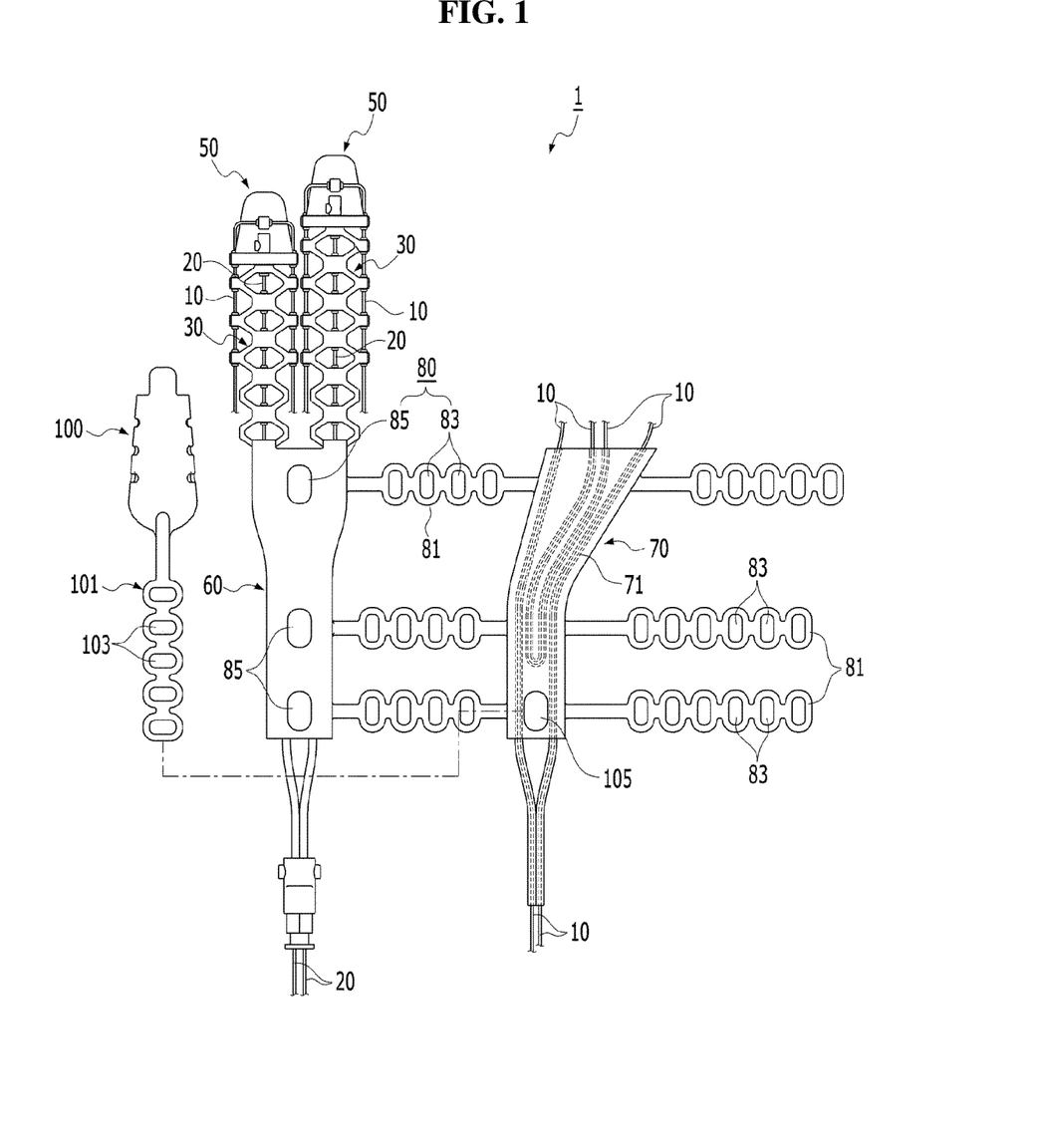
FIG. 1 is a view illustrating a configuration of a wearable hand robot according to an embodiment of the inventive concept.
Figure 2:
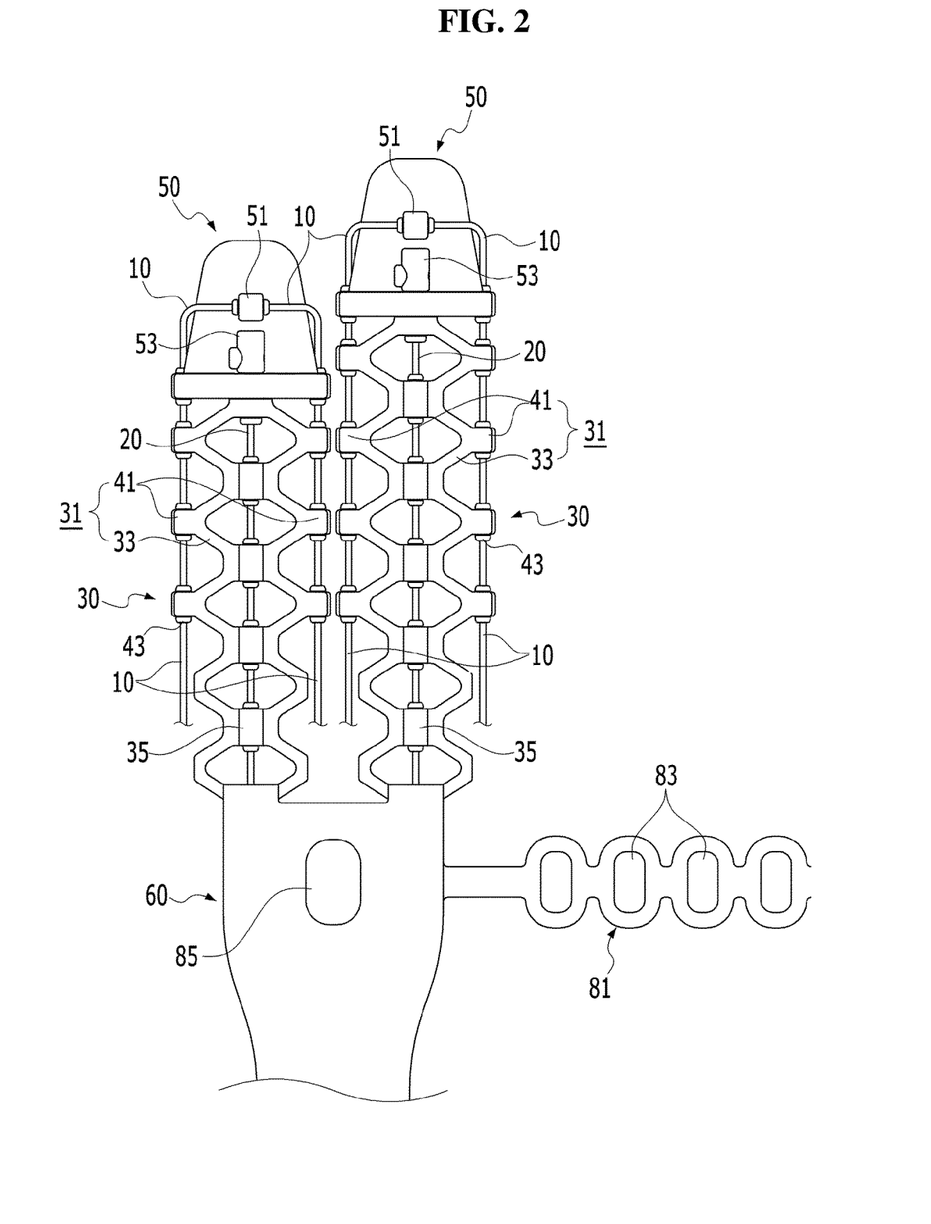
FIG. 2 is an enlarged view illustrating major components of FIG. 1.
Figure 3:
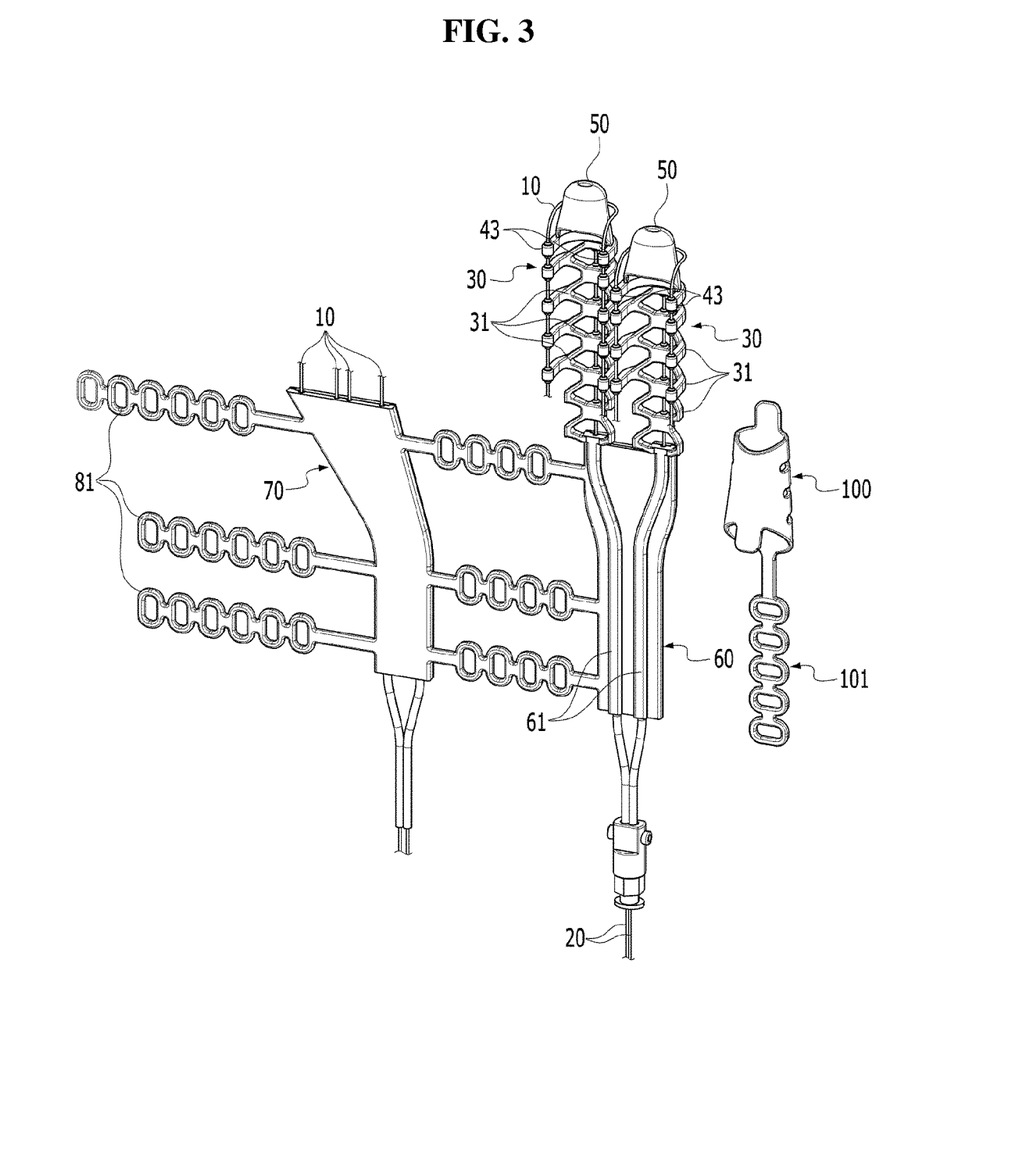
FIG. 3 is a rear perspective view of FIG. 1.

FIGS. 1 to 3 illustrate a wearable hand robot according to an embodiment of the inventive concept.

As illustrated in theses drawings, the wearable hand robot 1 according to the embodiment of the inventive concept includes a first wire 10, a second wire 20, a finger strap 30, a finger cap 50, a back-of-hand support part 60, and a palm support part 70.

Prior to description, it should be noted that in this embodiment, the finger strap 30 and the finger cap 50 will be described as being mounted on an index finger and a middle finger of a user, but without being limited thereto, the finger strap 30 and the finger cap 50 may be selectively mounted on the remaining fingers. Furthermore, the finger strap 30 and the finger cap 50 may be mounted on only one finger.

The first wire 10 is disposed to extend toward a distal end portion of a finger and then change an extension direction to a direction toward the root of the finger. In this embodiment, one first wire 10 is provided and performs an operation of being pulled or released by one first drive means not illustrated. That is, the first wire 10 in this embodiment is installed such that the first wire 10 passes through the palm support part 70, moves along the outsides of the finger strap 30 and the finger cap 50 that are mounted on the index finger, changes a moving direction to a direction toward the root of the index finger, enters the palm support part 70 via the finger strap 30 again, changes the moving direction to a direction toward the middle finger in the palm support part 70, moves along the outsides of the finger strap 30 and the finger cap 50 that are mounted on the middle finger, changes the moving direction to a direction toward the root of the middle finger, and passes through the palm support part 70 via the finger strap 30 again.

Accordingly, the two fingers may be simultaneously bent by the one first wire 10.

The second wire 20 is disposed to extend toward the distal end portion of the finger along the back of the finger. In this embodiment, two second wires 20 are provided and perform an operation of being independently pulled or released by different second drive means not illustrated. That is, the two second wires 20 are disposed on the index finger and the middle finger, respectively.

One second wire 20 passes through the back-of-hand support part 60 and is fixed to the outside of the finger cap 50 via the finger strap 30 mounted on the index finger. The other second wire 20 passes through the back-of-hand support part 60 and is fixed to the outside of the finger cap 50 via the finger strap 30 mounted on the middle finger.

Accordingly, the second wires 20 unfold the fingers by being pulled by the different second drive means. When the first wire 10 is pulled, the second wires 20 are released, and when the second wires 20 are pulled, the first wire 10 is released.

Meanwhile, the wearable hand robot 1 according to the embodiment of the inventive concept further includes a tension measurement sensor 11 for the first wire that is provided on a moving path of the first wire 10 and that measures tension acting on the first wire 10 and a tension measurement sensor 21 for the second wires that is provided on a moving path of the second wires 20 and that measures tension acting on the second wires 20.

Figure 4:
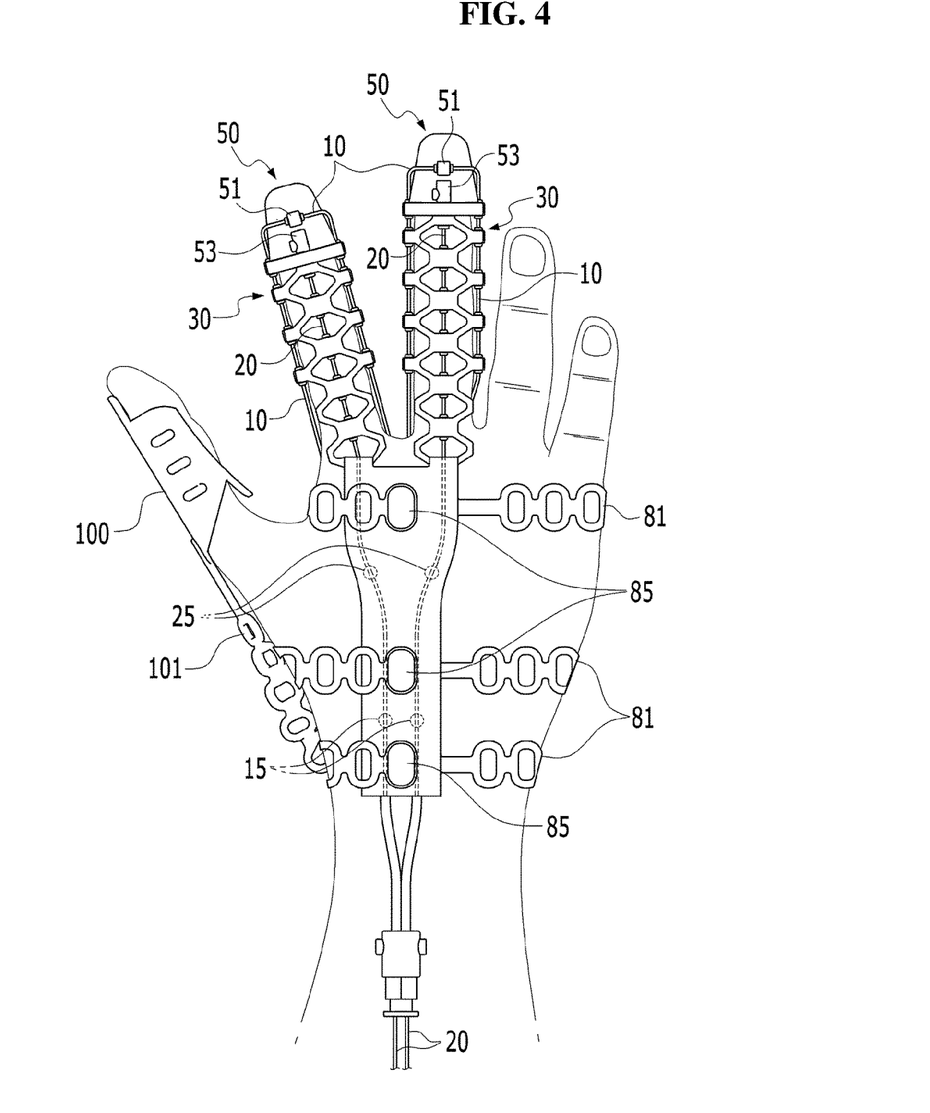
FIG. 4 is a view of the wearable hand robot of FIG. 1 as viewed in a direction toward the back of a hand.
Figure 5:
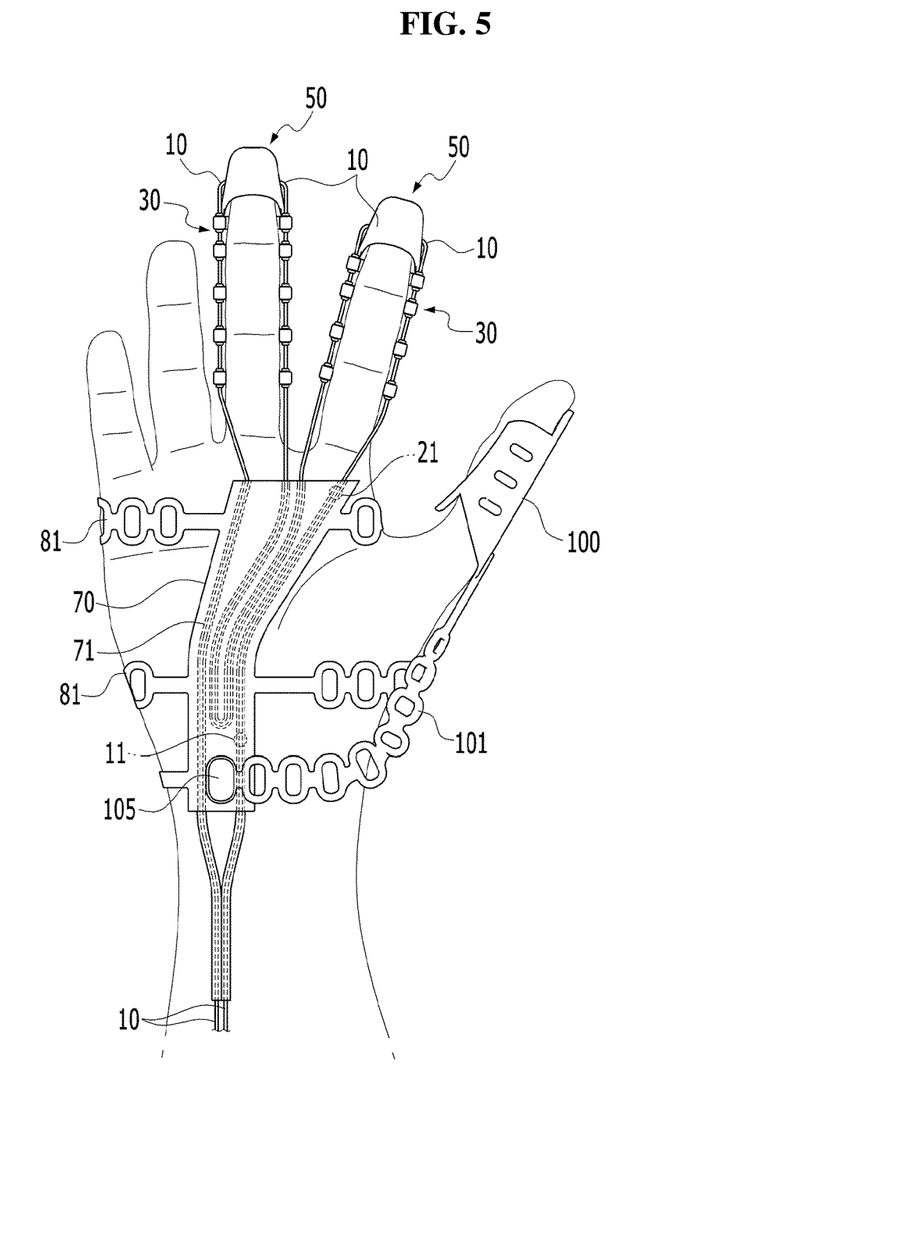
FIG. 5 is a view of the wearable hand robot of FIG. 1 as viewed in a direction toward the palm of the hand.

Here, although in this embodiment the tension measurement sensor 11 for the first wire is provided on the moving path of the first wire 10 in the palm support part 70 as illustrated in FIG. 5 and the tension measurement sensor 21 for the second wires is provided on the moving path of the second wires 20 in the back-of-hand support part 60 as illustrated in FIG. 4, the positions of the tension measurement sensor 11 for the first wire and the tension measurement sensor 21 for the second wires are not limited thereto. Furthermore, although in this embodiment the tension measurement sensors 11 and 21 are illustrated as being provided on the moving paths of the first wire 10 and the second wires 20, a tension measurement sensor, without being limited thereto, may be provided on only the moving path of one of the first wire and the second wires.

In addition, the wearable hand robot 1 according to the embodiment of the inventive concept further includes a joint angle measurement sensor 15 for the first wire that is provided on the moving path of the first wire 10 and that measures a joint angle of the finger by measuring the length by which the first wire 10 moves and a joint angle measurement sensor 25 for the second wires that is provided on the moving path of the second wires 20 and that measures a joint angle of the finger by measuring the length by which the second wires 20 move.

Here, although in this embodiment the joint angle measurement sensor 15 for the first wire is provided on the moving path of the first wire 10 in the palm support part 70 as illustrated in FIG. 5 and the joint angle measurement sensor 25 for the second wires is provided on the moving path of the second wires 20 in the back-of-hand support part 60 as illustrated in FIG. 4, the positions of the joint angle measurement sensor 15 for the first wire and the joint angle measurement sensor 25 for the second wires are not limited thereto. Furthermore, although in this embodiment the joint angle measurement sensors 15 and 25 are illustrated as being provided on the moving paths of the first wire 10 and the second wires 20, a joint angle measurement sensor, without being limited thereto, may be provided on only the moving path of one of the first wire and the second wires.

The finger strap 30 is formed by disposing a plurality of finger holders 31 in a row along the lengthwise direction of the finger. The finger strap 30 has the shape of straps mutually connected so as to be stretchable and bendable. The finger strap 30 may be formed to be stretchable such that depending on the length of the user's finger, the interval between the finger holders 31 adjacent to each other or the interval between the finger cap 50 and the finger holder 31 adjacent to each other is adjusted.

The finger holders 31 include a finger mounting part 33 and a pair of finger grips 41.

The finger mounting part 33 has a cross-sectional shape perforated in a rhombic shape. The plurality of finger mounting parts 33 are mutually connected so as to be stretchable along the lengthwise direction of the finger and are mutually connected so as to be bendable when the finger is moved. Here, although the finger mounting parts 33 in this embodiment are illustrated as having the cross-sectional shape perforated in the rhombic shape, the finger mounting parts 33, without being limited thereto, may have various cross-sectional shapes such as a circular shape, an oval shape, a polygonal shape, and the like.

A second wire passage 35 through which the second wire 20 moves is formed in the center of the finger mounting part 33 along the lengthwise direction of the finger. In this embodiment, a tube through which the second wire 20 is inserted is provided as the second wire passage 35. Accordingly, the second wire 20 is inserted through a plurality of second wire passages 35 and is disposed on the back of the finger while forming a straight line along the lengthwise direction of the finger.

The pair of finger grips 41 protrude from the finger mounting part 33 so as to be opposite to each other, for example, protrude from the finger mounting part 33 so as to be symmetric to each other with respect to the second wire passage 35 therebetween. The finger holder 31 has an arc-shaped cross-section so as to grip the finger while partially surrounding the finger. The pair of finger grips 41 are preferably formed of an elastically deformable material such that when the finger is gripped, the pair of finger grips 41 move away from each other while sliding on opposite side surfaces of the finger and thereafter move toward each other by an elastic force thereof to make close contact with the finger while partially surrounding the finger.

Furthermore, a first wire passage 43 through which the first wire 10 moves is formed in each finger grip 41 so as to be parallel with the second wire passage 35. Accordingly, the first wire 10 is inserted through a plurality of first wire passages 43 disposed in a row and is disposed on opposite sides of the finger, with the back of the finger therebetween while forming a straight line along the lengthwise direction of the finger. Thus, through each finger grip 41 of the finger strap 30, each finger holder 31 may be simply and conveniently mounted on the back of the finger from above the back of the finger.

The finger cap 50 has a thimble shape and is mounted on the distal end portion of the finger to surround the distal end portion of the finger.

A wire direction changing part 51 for changing the moving direction of the first wire 10 is provided on the outside of the finger cap 50, for example, on the outside of the finger cap 50 that forms the same plane with the back of the finger. Furthermore, a wire fixing part 53 to which a distal end portion of the second wire 20 is fixed is provided between the wire direction changing part 51 and the finger strap 30. Wire fixing part 53 is in line with the second wire passage 35.

Accordingly, the moving paths of the first wire 10 and the second wire 20 are not formed inside the finger cap 50 in the inventive concept, and therefore the user may have a tactile sensation when wearing the finger cap 50.

To support the back of the user's hand, the back-of-hand support part 60 is disposed on the back of the hand. One end portion of each of the finger straps 30 mounted on the index finger and the middle finger is connected to the back-of-hand support part 60.

Furthermore, the back-of-hand support part 60 is equipped with second wire guides 61 that guide movement of the second wires 20. The second wire guides 61 have a tubular shape through which the second wires 20 are inserted so as not to be exposed.

The palm support part 70 supports the palm of the user's hand. The palm support part 70 is equipped with a first wire guide 71 that guides movement of the first wire 10. The first wire guide 71 has the shape of a through-hole through which the first wire 10 is inserted so as not to be exposed.

Meanwhile, the back-of-hand support part 60 and the palm support part 70 are mounted on the hand by a mounting means 80. In this embodiment, bands 81 and locking protrusions 85 are included as the mounting means 80.

The bands 81 have a strap shape with a predetermined length, and three bands 81 are horizontally disposed at intervals in the lengthwise direction of the back-of-hand support part 60. Each band 81 connects the back-of-hand support part 60 and the palm support part 70 in a direction across the lengthwise direction of the finger and is disposed to extend from one side of the palm support part 70. Furthermore, a plurality of locking recesses 83 are formed through the band 81 along the lengthwise direction of the band 81. Although the locking recesses 83 have a cross-sectional shape of a long hole, the locking recesses 83 may have a cross-sectional shape such as a circular shape, an oval shape, a polygonal shape, or the like other than the long hole.

The locking protrusions 85 have a cross-sectional shape corresponding to the locking recesses 83 and protrude from the back-of-hand support part 60. Each locking protrusion 85 is selectively fit into one of the plurality of locking recesses 83 formed on the band 81.

Accordingly, the mounting means 80 may mount the back-of-hand support part 60 and the palm support part 70 on the user's hand by mutually connecting the back-of-hand support part 60 and the palm support part 70.

Here, although in this embodiment the locking protrusions 85 are illustrated as protruding from the back-of-hand support part 60, the locking protrusions 85, without being limited thereto, may protrude from the palm support part 70. Further, although in this embodiment the locking recesses 83 and the locking protrusions 85 are provided as the mounting means 80, the mounting means 80, without being limited thereto, may be implemented with Velcro cloth, a double-sided tape, or the like.

Meanwhile, the wearable hand robot 1 according to the embodiment of the inventive concept further includes a finger tube 100 for a thumb that is attached to or detached from the user's thumb.

The finger tube 100 for the thumb serves to receive the thumb and fix the thumb during finger motion.

A band 101 for the finger tube is provided on one side of the finger tube 100 for the thumb. The band 101 for the finger tube has a strap shape with a predetermined length and is disposed to extend along the lengthwise direction of the band 101 for the finger tube. Furthermore, a plurality of auxiliary locking recesses 103 are formed through the band 101 for the finger tube along the lengthwise direction of the band 101 for the finger tube. Although the auxiliary locking recesses 103 have a cross-sectional shape of a long hole, the auxiliary locking recesses 103 may have a cross-sectional shape such as a circular shape, an oval shape, a polygonal shape, or the like other than the long hole.

An auxiliary locking protrusion 105 has a cross-sectional shape corresponding to the auxiliary locking recesses 103 and protrudes from the palm support part 70. The auxiliary locking protrusion 105 is selectively fit into one of the plurality of auxiliary locking recesses 103 formed on the band 101 for the finger tube.

Accordingly, the finger tube 100 for the thumb may be mounted on the user's hand by the auxiliary locking recesses 103 and the auxiliary locking protrusion 105.

Here, although in this embodiment the auxiliary locking protrusion 105 is illustrated as protruding from the palm support part 70, the auxiliary locking protrusion 105, without being limited thereto, may protrude from the back-of-hand support part 60. Further, although in this embodiment the auxiliary locking recesses 103 and the auxiliary locking protrusion 105 are provided as the mounting means 80, the mounting means 80, without being limited thereto, may be implemented with Velcro cloth, a double-sided tape, or the like.

Hereinafter, operation of the above-configured wearable hand robot 1 according to the embodiment of the inventive concept will be described.

Figure 6:
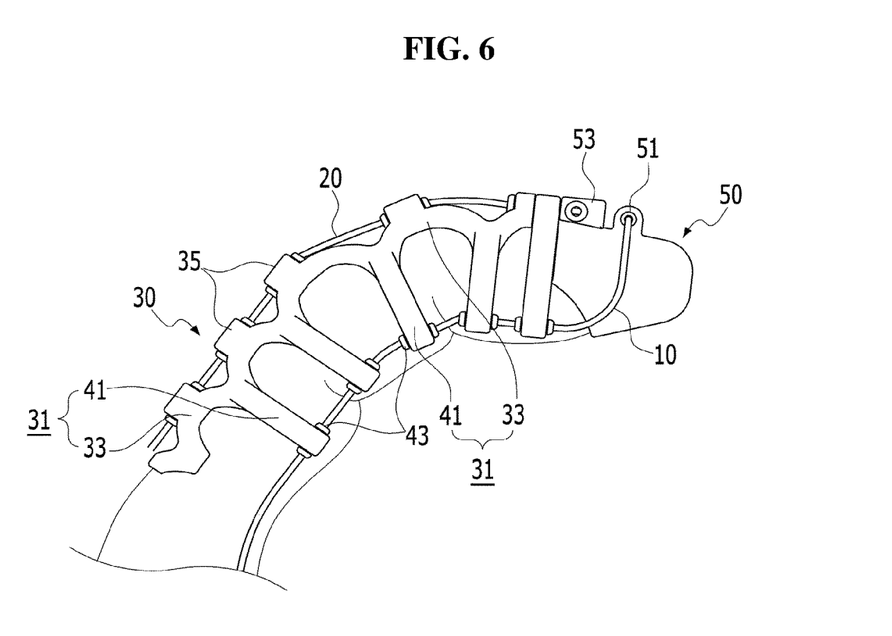
FIG. 6 is a side view illustrating major parts in a state in which the wearable hand robot of FIG. 1 is worn on a finger.

As illustrated in FIGS. 4 to 6, the finger caps 50 are mounted on the index finger and the middle finger of the user. In addition, the finger tube 100 for the thumb is mounted on the thumb.

Further, from above the backs of the index finger and the middle finger, the finger holders 31 of the finger straps 30 are mounted on the backs of the fingers along the lengthwise directions of the fingers. At this time, the finger grips 41 of the finger holders 31 partially surround the fingers, and the finger holders 31 are mounted on the backs of the fingers.

At this time, the finger straps 30 fit the user's fingers while being lengthened or shortened depending on the lengths of the user's fingers.

Next, the back-of-hand support part 60 is disposed on the back of the user's hand, and the palm support part 70 is disposed on the palm of the user's hand. Thereafter, the back-of-hand support parts 60 and the palm support part 70 are mounted on the user's hand by adjusting the length of the mounting means 80 depending on the size of the user's hand.

Further, the band 101 for the finger tube is fixed by fitting the auxiliary locking protrusion 105, which is formed on the palm support part 70, into one auxiliary locking recess 103 among the plurality of auxiliary locking recesses 103, which are formed on the band 101 for the finger tube, depending on the length of the user's thumb.

Meanwhile, the first wire 10 is installed such that the first wire 10 passes through the palm support part 70, moves along the outsides of the finger strap 30 and the finger cap 50 that are mounted on the index finger, changes the moving direction to the direction toward the root of the index finger by the wire direction changing part 51 provided on the finger cap 50, enters the palm support part 70 again via the finger strap 30 mounted on the index finger, changes the moving direction to the direction toward the middle finger in the palm support part 70, moves along the outsides of the finger strap 30 and the finger cap 50 that are mounted on the middle finger, changes the moving direction to the direction toward the root of the middle finger by the wire direction changing part 51 provided on the finger cap 50, and passes through the palm support part 70 via the finger strap 30 again.

One of the second wires 20 passes through the back-of-hand support part 60 and is fixed to the wire fixing part 53, which is provided on the outside of the finger cap 50, via the finger strap 30 mounted on the index finger, and the other second wire 20 passes through the back-of-hand support part 60 and is fixed to the wire fixing part 53, which is provided on the outside of the finger cap 50, via the finger strap 30 mounted on the middle finger.

In the state in which the wearable hand robot 1 according to the embodiment of the inventive concept is completely mounted on the user's hand as described above, the first wire 10 and the second wires 20 remain released before operation of an actuator, and therefore the user's hand is in an unfolded state.

In this state, the fingers are located adjacent to an object that the user wants to hold.

Next, the user bends the thumb to bring the finger tube 100 for the thumb into contact with the object and bends the index finger and the middle finger toward the object by pulling the first wire 10, which passes through the finger straps 30 and the finger caps 50 that are mounted on the index finger and the middle finger, by the first drive means (not illustrated). At this time, because the first wire 10 sequentially passes through the index finger and the middle finger, the index finger is first bent toward the object when the first wire 10 is pulled, and the middle finger is bent toward the object without additional bending of the index finger when the index finger is brought into contact with the object. When the fingers are bent by the first wire 10, each finger strap 30 is stretched while being bent together along joints of the finger and remains brought into contact with the user's finger. Through this process, the thumb, the index finger, and the middle finger of the user may hold the object.

Meanwhile, as the first wire 10 is pulled, the second wires 20 are released by the second drive means (not illustrated) so as not to interfere with the operation of the first wire 10.

While releasing the pulled first wire 10 by operating the first drive means again, the user operates the second drive means to pull the second wires 20, which pass through the finger caps 50 and the finger straps 30 mounted on the index finger and the middle finger, to unfold the bent fingers.

As described above, the wearable hand robot 1 according to the inventive concept has an improved connecting structure between the wires pulled or released and the finger caps 50. That is, the first wire 10 and the second wires 20 press the user's hand while being pulled or released by the first drive means and the second drive means through the finger straps 30 and the finger caps 50 through which the first wire 10 and the second wires 20 pass, the back-of-hand support part 60, and the palm support part 70. Accordingly, penetration of the first wire 10 and the second wires 20 into the user's skin or an abrasion due to friction of the first wire 10 and the second wires 20 with the user's skin may be prevented.

Furthermore, as the first wire 10 and the second wires 20 are disposed on the outsides of the finger caps 50 without being disposed inside the finger caps 50, the insides of the finger caps 50 for accommodating the wires do not need to have a double or triple structure. Accordingly, simplification of the structures of the finger caps 50 and an improvement in a wearing sensation may be achieved, and the user may stably move the fingers while having a tactile sensation.

In addition, as the finger holders 31 are able to be mounted on finger joints as well as finger knuckles, the finger straps 30 are not raised off the finger knuckles when the fingers are moved. Accordingly, the fingers may be stably moved while the finger straps 30 are not easily separated from the fingers.

Meanwhile, in the above-described embodiment, it has been described that the one first wire sequentially passes through the finger straps and the finger caps mounted on the index finger and the middle finger. However, although not illustrated as another embodiment, the first wire may be constituted by two wires, one of which is installed to independently pass through the finger strap and the finger cap that are mounted on the index finger, and the other of which is installed to independently pass through the finger strap and the finger cap that are mounted on the middle finger. The first drive means may separately pull each of the first wires to bend a finger on which the corresponding first wire is installed.

Furthermore, the first wire may be constituted by a single wire and may be disposed to sequentially pass through finger straps and finger caps mounted on the thumb, the index finger, and the middle finger. When the first wire is pulled, the thumb may be first bent toward an object. When the thumb is brought into contact with the object, the thumb may not be bent any more, and the index finger and the middle finger may be sequentially bent toward the object to hold the object.

According to the inventive concept, the wearable hand robot has an improved connecting structure between the wires pulled or released and the finger cap, thereby preventing an injury to a user's hand by the wires, achieving simplification of the structure of the finger cap and an improvement in a wearing sensation, and enabling the user to stably move a finger while having a tactile sensation.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A wearable hand robot comprising:
   at least one first wire disposed to extend toward a distal end portion of a finger and change an extension direction to a direction toward a root of the finger;
   a second wire disposed to extend toward the distal end portion of the finger along the back of the finger;
   a finger strap having a plurality of finger holders mutually connected along a lengthwise direction of the finger, wherein each of the plurality of finger holders includes a finger mounting part mounted on the back of the finger and configured to form a second wire passage through which the second wire moves and a pair of finger grips protruding from the finger mounting part so as to be opposite to each other and having a first wire passage formed therein through which the first wire moves, the pair of finger grips being configured to grip the finger while partially surrounding the finger;
   a finger cap mounted on the distal end portion of the finger, wherein the finger cap has a wire direction changing part that is provided on the outside of the finger cap and to which the first wire is coupled so as to be exposed, the wire direction changing part being configured to change a moving direction of the first wire, and a wire fixing part that is in line with the second wire passage between the wire direction changing part and the finger strap and to which a distal end portion of the second wire is fixed;
   a back-of-hand support part including a second wire guide configured to guide movement of the second wire, the back-of-hand support part being supported on the back of a hand; and
   a palm support part including a first wire guide configured to guide movement of the first wire, the palm support part being supported on a palm of the hand,
   wherein the finger holders are mounted on finger knuckles and finger joints such that the finger strap is not separated from the finger knuckles when the finger is moved,
   wherein an end portion of the first wire has a "U" shape through the wire direction changing part, which is positioned at a bottom of the "U" shape, is coupled to the outside of the finger cap, and is configured to be located above a nail of the finger,
   wherein the distal end portion of the second wire is fixed to the wire fixing part, which is coupled to the outside of the finger cap, and is configured to be located above the nail of the finger, and
   wherein the wire fixing part is positioned inside the "U" shape of the end portion of the first wire and is farther from a distal end of the finger cap than the wire direction changing part, and the second wire is not intersected with the first wire.

2. The wearable hand robot of claim 1, further comprising:
   a mounting means configured to mount the back-of-hand support part and the palm support part on the hand.

3. The wearable hand robot of claim 2, wherein the mounting means includes:
   a band configured to connect the back-of-hand support part and the palm support part, the band having a plurality of locking recesses formed through the band; and
   a locking protrusion protruding from the back-of-hand support part or the palm support part, the locking protrusion being selectively fit into the plurality of locking recesses of the band.

4. The wearable hand robot of claim 1, further comprising:
a finger tube for a thumb, the finger tube being attached to or detached from the thumb;
a band for the finger tube, the band having a plurality of auxiliary locking recesses formed therein, wherein the band supports the finger tube for the thumb; and
an auxiliary locking protrusion protruding from the back-of-hand support part or the palm support part, the auxiliary locking protrusion being selectively fit into the plurality of auxiliary locking recesses of the band for the finger tube.

5. The wearable hand robot of claim 1, wherein the finger strap includes two finger straps mounted on an index finger and a middle finger of a user, respectively, and
wherein the first wire is installed to pass through finger caps and the finger straps mounted on the index finger and the middle finger.

6. The wearable hand robot of claim 1, wherein the finger strap is formed to be stretchable such that an interval between the finger holders adjacent to each other or an interval between the finger cap and the finger holder adjacent to each other is adjusted depending on a length of a user's finger.

7. The wearable hand robot of claim 1, further comprising:
a tension measurement sensor provided on a moving path of at least one of the first wire and the second wire and configured to measure tension acting on at least one of the first wire and the second wire.

8. The wearable hand robot of claim 1, further comprising:
a joint angle measurement sensor provided on a moving path of at least one of the first wire and the second wire and configured to measure a joint angle of the finger depending on a length by which at least one of the first wire and the second wire moves.

* * * * *